US00PP18941P2

(12) United States Plant Patent
Higaki

(10) Patent No.: US PP18,941 P2
(45) Date of Patent: Jun. 17, 2008

(54) *LAVANDULA* PLANT NAMED 'DREAM'

(50) Latin Name: *Lavandula stoechas*
Varietal Denomination: Dream

(75) Inventor: Harrison Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 11/646,839

(22) Filed: Dec. 27, 2006

(51) Int. Cl.
*A01H 5/00* (2006.01)

(52) U.S. Cl. ..... Plt./445

(58) Field of Classification Search ..... Plt./445, Plt./263

See application file for complete search history.

*Primary Examiner*—Wendy C. Haas
(74) *Attorney, Agent, or Firm*—James Cypher; Charles R. Cypher

(57) ABSTRACT

A new and distinct cultivar of *Lavandula stoechas* L. named 'Dream' originated as seedling from a controlled cross between *Lavandula stoechas* L. 'Cellers' and an unnamed *Lavandula stoechas* L. The terminal inflorescences of the cultivar 'Dream' have showy top bracts which are R.H.S. 76A (violet group) at maturity. 'Dream' also has a compact growth habit.

4 Drawing Sheets

Botanical classification: *Lavandula stoechas* L. 'Dream'. Variety denomination: 'Dream'.

BACKGROUND OF THE INVENTION

The present invention relates to a new and distinct cultivar of *Lavandula stoechas* named 'Dream' by the assignees.

The new cultivar originated as a seedling from a controlled cross between *Lavandula stoechas* L. 'Cellers' and an unnamed *Lavandula stoechas* L. cultivar.

The new variety has been asexually propagated by cuttings through three generations, and the characteristics of the new cultivar have been determined to be fixed and stable.

SUMMARY OF THE INVENTION

The new variety of *Lavandula stoechas* L. is characterized by its compact growth habit, flower color and suitably for commercial cultivation.

BRIEF DESCRIPTION OF THE DRAWINGS

The accompanying drawings consist of color photographs illustrate the distinguishing characteristics of the new variety. All photographs were taken using conventional photographic techniques.

BOTANICAL DESCRIPTION OF THE PLANT

Figure 1:
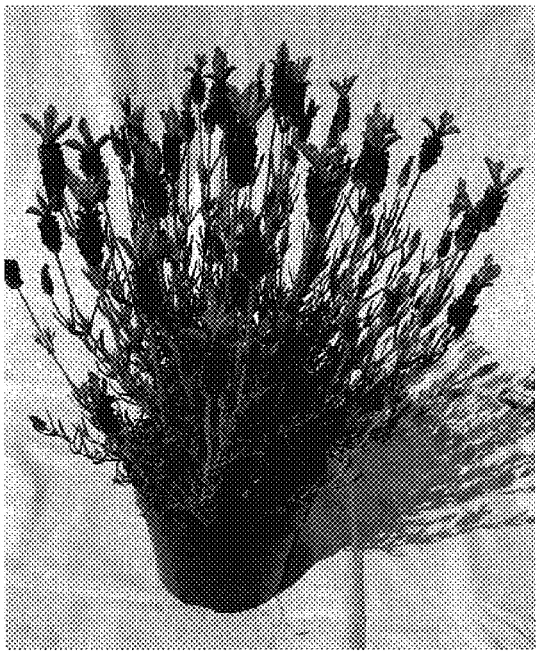
FIG. 1 is a view of the entire plant showing its compact growth habit.
Figure 2:
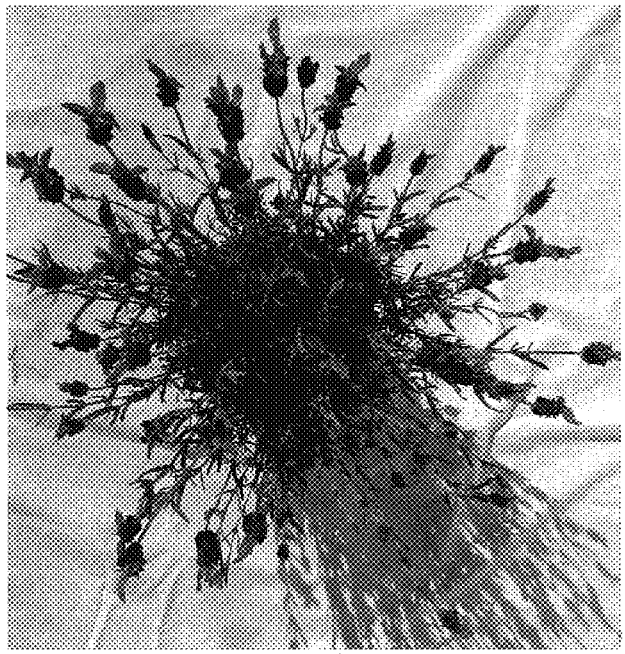
FIG. 2 is a top view of the entire plant showing its compact growth habit.
Figure 3:
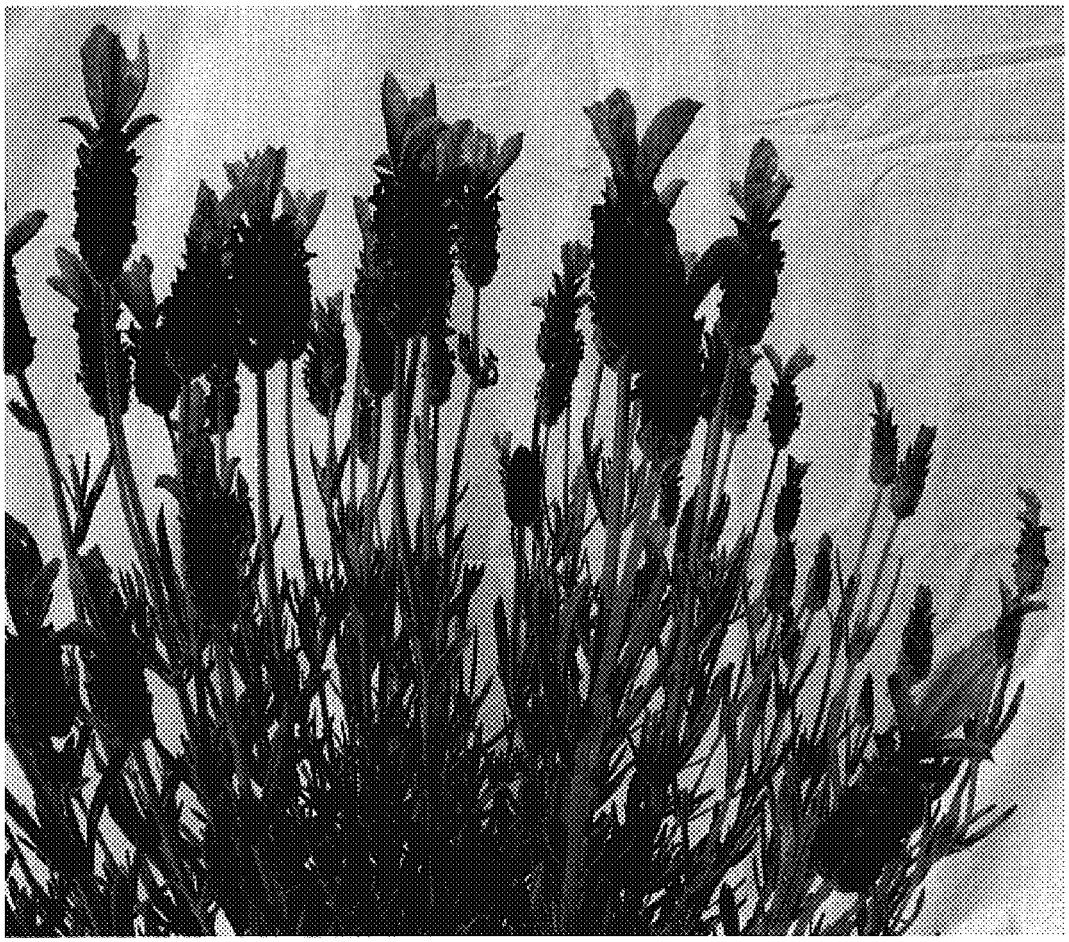
FIG. 3 is a close-up view of a number of terminal spikes on a single plant of the new variety, showing mature inflorescences.
Figure 4:
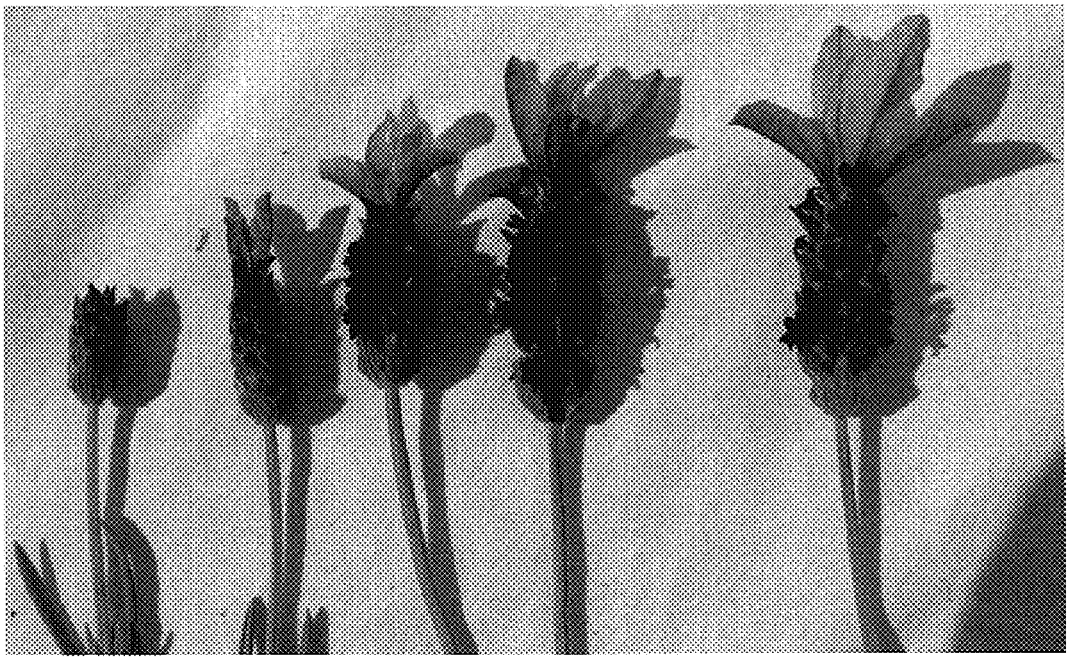
FIG. 4 is a close-up view of a number of different inflorescences at different stages. The youngest inflorescence is on the left of the drawing, and the oldest is on the right side of the drawing.
Figure 5:
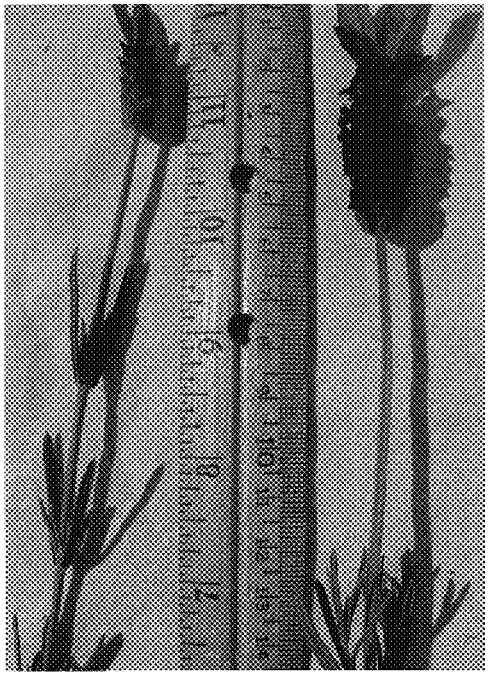
FIG. 5 is a close-up view of a pair of stems with terminal inflorescences. The stem and inflorescence on the left of the drawing is younger than the stem and inflorescence on the right of the drawing.
Figure 6:
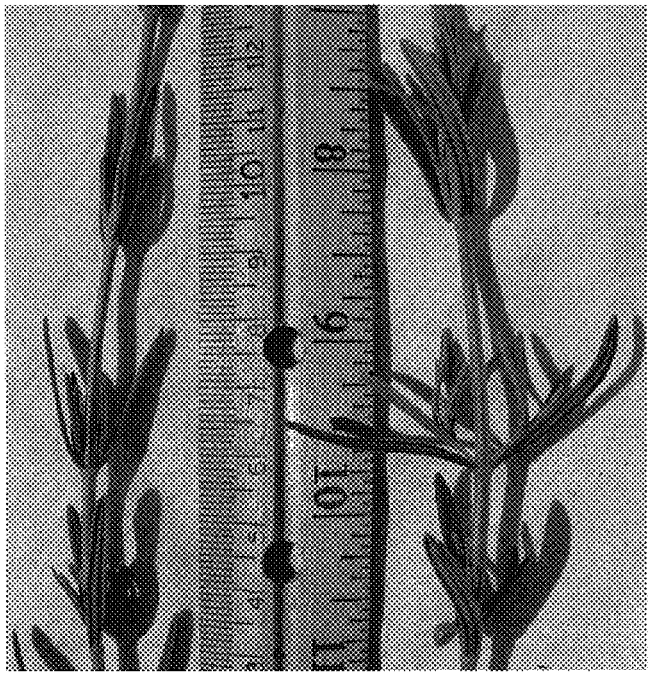
FIG. 6 is a close-up view of a pair of stems. The stem on the left of the drawing is younger than the stem and inflorescence on the right of the drawing.
Figure 7:
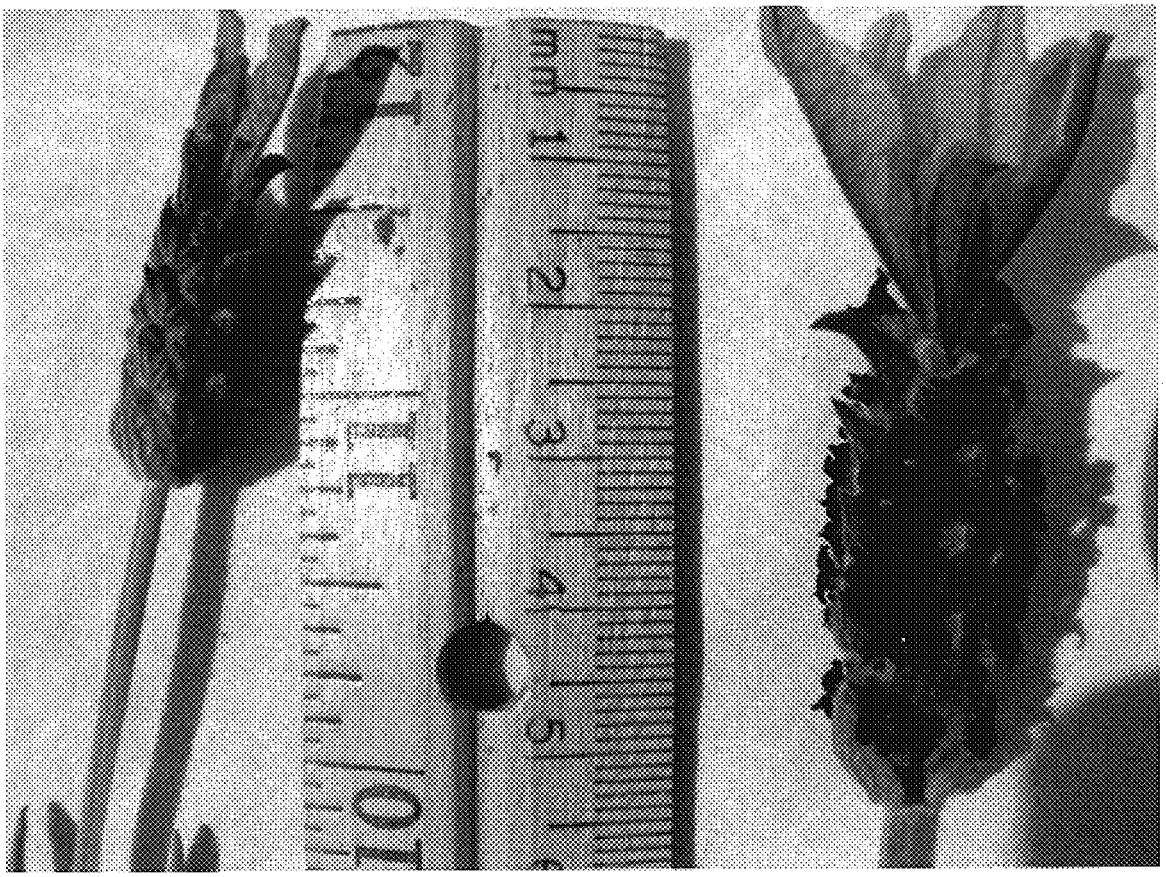
FIG. 7 a close-up view of a pair of terminal inflorescences. The stem and inflorescence on the left of the drawing is younger than the stem and inflorescence on the right of the drawing.

The following is a detailed description of the new variety. The new variety has not been observed under all possible environmental conditions. Color designation and other values may deviate slightly from the stated values from flowering to flowering, but the deviations will be within the range expected from varying environmental, seasonal and cultural conditions. Color designations were made according to the R.H.S. Color Chart published by The Royal Horticultural Society of London, England.

The plants observed were grown in 6" pots. The plants were approximately eight months old.

The tallest plants were approximately 12" high.

The following description is based on observations of optimally fertilized plants.

The plants were grown outside at a commercial nursery in Half Moon Bay, Calif. Temperatures in Half Moon Bay on average range from 55 to 65 degrees Fahrenheit in the summer months, and from 45 to 55 degrees Fahrenheit in the winter months. The observed plants were pinched back once.

Cuttings were taken from mature plants in the winter and placed in cells, and were kept under glass during root initiation. Root initiation occurred in approximately 3 weeks, after which the plants where moved outside for seven weeks. Plants were than transplanted to 6" pots, where they were grown outside. Plant were pinched once. The plants were well fertilized.

THE PLANT

Name: *Lavandula stoechas* L. 'Dream'. Parents: Controlled hybridization of *Lavandula stoechas* L. 'Cellers' and an unnamed *Lavandula stoechas* L. Classification: Family — Labiatae, Genus — *Lavandula stoechas* L.

Type: Aromatic, perennial shrub that grows well in well-drained soils in full sun. Form: Mounded and semi-open with erect, assending flower spikes. Height: 12". Diameter: 12".

Stems:

*General.*—Stems branch easily. Stems are erect.

*Shape.*—Young stems are 1 mm wide and have a square cross-section, older woody stems are 3 mm wide, and oldest stem at base of plant is 6 mm wide and round.

*Color.*—Young stems are 138 C (green group) or 145B (yellow-green group) (and darker than stock) and relatively newly woody portions of stem are 199 C (grey-brown group).

Foliage:

*Arrangement.*—Leaves are paired and opposite, with leaves at adjacent nodes on the stem set at substantially 90 degree angles to each on the square cross-section stems. The first node below the terminal inflorescence occurs anywhere from 45 mm to 85 mm. Lower nodes are spaced anywhere from 20 mm to 40 mm, whith the upper nodes on the stem being spaced farther apart.

*Shape.*—Narrow, linear leaves that lack a petiole. The lateral leaf margins are reflexed, rolling under the underside of the leaf. Leaves have a large central vein that is, recessed on the upper side.

*Length.*—The longest leaves are in the node just below the terminal inflorescence, and these leaves generally range from 27 mm to 30 mm long.

*Width.*—Leaves are 3 mm wide.

*Color.*—Leaves are 138B (green group) on the upper sides and 138C (green group) on their undersides.

*Texture.*—canescent.

THE INFLORESCENCE AND FLORETS

*General.*—Terminal spike of a plurality of individual florets arranged in groups with corresponding scales.

*Size of inflorescences.*—The inflorescence ranges in height from 17 mm to 30 mm, not including the top bracts.

*Top bracts.*—Top bracts range in size from 20 mm to 27 mm and range in width from 6 mm to 7 mm. Number of top bracts ranges from 5 to 7. Top bract color is R.H.S. 76A (violet group), both sides.

Scales — 8 mm tall and 6 mm wide. On the side away from the stems the veins are very prominent and are 138 B (green group) as is the tip of the scale. Scales have curly white hairs. Easily 20 scales with flowers in inflorescence, and generally five florets associated with a scale. Scales alternate like leaves on the stem in opposing pairs.

Florets:

*General.*—The corolla tube is two-lipped with upper lip being two lobed and the lower lip being three lobed. Stamens exserted with respect to the corolla. Anthers are 15A (yellow-orange group) or 21 A (yellow-orange group). Petal diameter is 4–5 mm. Style is 86B. Style is lower.

*Size.*—5 mm to 7 mm long tube of sepals, hairy sepals. Color of sepals is 138 D (green group) or 145B. Total length of flower is 10 mm.

*Color.*—Top of Corolla is 86A (violet group), while base is 155D white group, while stock bast 76D (purple group).

Fragrance: A mix of typical lavender scent and a pungent rosemary scent.

I claim:

1. A new and distinct *Lavandula stoechas* L. plant named 'Dream' substantially as herein shown and described.

* * * * *